United States Patent [19]

Hardy, Jr. et al.

[11] Patent Number: 4,552,148
[45] Date of Patent: Nov. 12, 1985

[54] ANASTOMOTIC DEVICE

[75] Inventors: Thomas G. Hardy, Jr., Columbus; A. L. Kaganov, Stamford; W. G. Pace, Columbus, all of Ohio

[73] Assignee: American Cyanamid Company, Stamford, Conn. ; a part interest

[21] Appl. No.: 583,956

[22] Filed: Feb. 27, 1984

Related U.S. Application Data

[63] Continuation of Ser. No. 287,500, Jul. 27, 1981, Pat. No. 4,467,804, which is a continuation-in-part of Ser. No. 198,448, Oct. 20, 1980, abandoned.

[51] Int. Cl.$^4$ .............................................. A61B 17/11
[52] U.S. Cl. ................................................. 128/334 C
[58] Field of Search ............... 128/334 C, 334 R, 346; 227/DIG. 1

[56] References Cited

U.S. PATENT DOCUMENTS

| | | | |
|---|---|---|---|
| 1,470,707 | 10/1923 | Bates | 128/334 |
| 2,428,918 | 10/1947 | Miller | 128/334 |
| 2,453,056 | 11/1948 | Zack | 128/334 |
| 2,638,901 | 5/1953 | Sugarbaker | 128/334 |
| 3,166,072 | 1/1965 | Sullivan | 128/346 X |
| 3,254,650 | 6/1966 | Collito | 128/334 |
| 3,496,939 | 2/1970 | Odiaga et al. | 128/334 |
| 3,771,526 | 11/1973 | Rudie | 128/334 C |
| 3,974,835 | 8/1976 | Hardy | 128/334 C |
| 4,055,186 | 10/1977 | Leveen | 128/334 C |
| 4,154,241 | 5/1979 | Rudie | 128/334 C |
| 4,182,339 | 1/1980 | Hardy | 128/334 R |
| 4,294,255 | 10/1981 | Geroc | 128/334 C |

FOREIGN PATENT DOCUMENTS 357306  8/1922  Fed. Rep. of Germany ... 128/334 C Primary Examiner—Michael H. Thaler

[57] ABSTRACT

An anastomotic device for receiving the free ends of anatomic tubular structures to be anastomosed, the device having a pair of ring members for securement to the free end of each of the tubular members to be anastomosed and the ring members having annular connecting structures which mate with each other to connect the ring members. Novel securement structures are associated with the annular connecting structures to enable the securement of the ring members in a fixed relationship at a predetermined distance from each other. Structure is provided to connect each tubular member free end over a ring member so that the free ends are positioned contiguous to each other around the connecting structures to enable the ends to grow together and approximate the outer surface of the tubular member.

11 Claims, 22 Drawing Figures

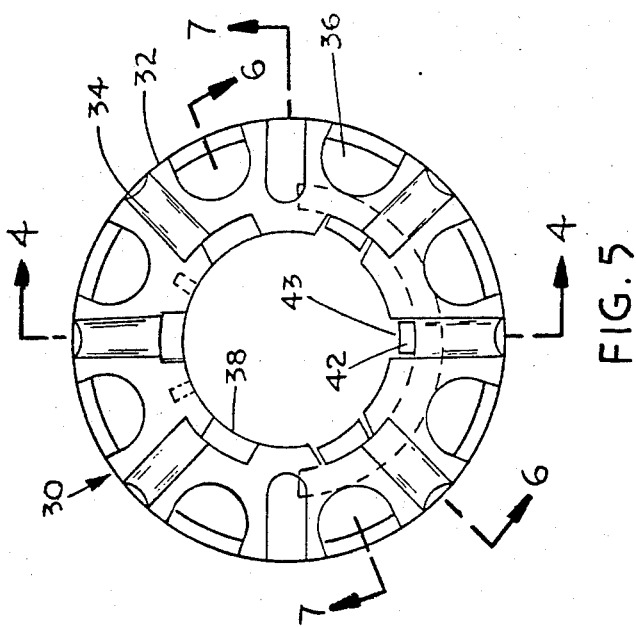
FIG. 5
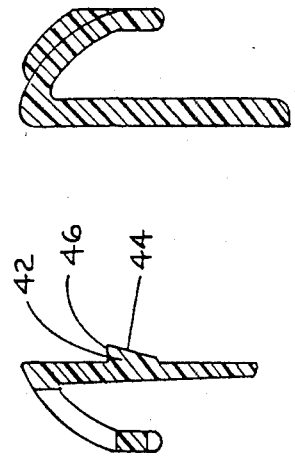
FIG. 7
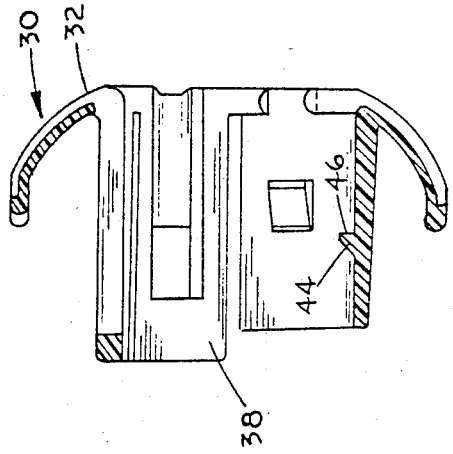
FIG. 4
FIG. 6
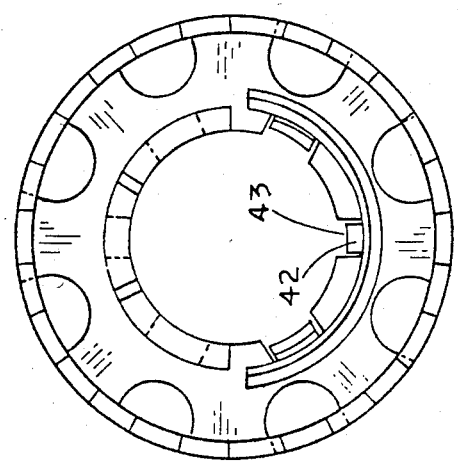
FIG. 2
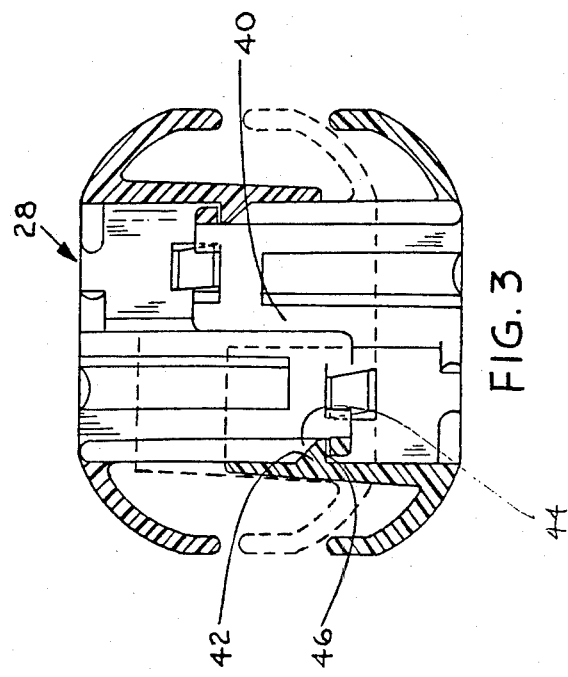
FIG. 3

ANASTOMOTIC DEVICE

CROSS REFERENCE TO RELATED APPLICATION

This application is a continuation of our co-pending application Ser. No. 287,500 filed Jul. 27, 1981, U.S. Pat. No. 4,467,804, which is a continuation-in-part of Ser. No. 198,448 filed Oct. 20, 1980, abandoned.

BACKGROUND OF THE INVENTION

This invention relates to an anastomotic device and particularly to a surgical clamp for using same for anastomosing one hollow or tubular member to another such as, for example, the severed ends of the intestine after surgery.

An anastomotic device formed of separate ring members having a plurality of fenestrated projections connected by a separate coupling tube is disclosed in U.S. Pat. No. 3,974,835. A similar device formed of a singular pliable, unitary cylindrical sleeve made of knit fabric is disclosed in U.S. Pat. No. 4,182,339.

In the anastomotic device disclosed in the first-referenced patent, the free ends of the tube to be joined are tied to the separate ring members at the fenestrated projections, and the singular coupling tube connects the two ring members to engage the tubular ends in a relationship that will enable them to grow together permanently and thereby approximate the diameter of the outer surface of the tubular member.

In U.S. Pat. No. 4,182,339, the unitary, knit cylindrical sleeve has its ends rolled outwardly upon themselves to form relatively firm ring members in spaced relationships which are then connected to the ends of the tubular members in a configuration that will enable these members to grow together.

Present medical techniques for joining the severed ends of the intestine include stitching the severed ends of the vessel together or using stapling instruments, all of which have some inherent disadvantages. Technical difficulties in utilizing suturing techniques often occur because of the inaccessibility of one or both of the ends or the time involved for anastomosis. Stapling instruments also have some inherent disadvantages because of technical problems associated with the position of severed vessels within the patient.

The above-referenced patents disclose means to draw the ends of the tubular members together by either turning or rolling these members inwardly to facilitate healing because they enable the ends to rest in a contiguous relationship. Other techniques involve devices like those disclosed in U.S. Pat. Nos. 3,496,939 and 3,254,640; however, the devices illustrated therein are somewhat expensive and complicated, and require very precise and careful handling if they are to be correctly utilized.

It is desirable that a nonpermanent connector or junction device be used to join the vessel ends in anastomotic surgery, since a permanent connector will tend to prevent the changes in diameter which are necessary for the proper functioning of the intestine. Any foreign substance used in anastomotic surgery ideally should disintegrate in a relatively short period of time once healing of the vessel ends is initiated.

The present invention has been developed to meet the current requirements of anastomotic surgery and to provide a safe, relatively inexpensive and easy-to-use anastomotic device. It is a disintegratable anastomotic article which has locking features to accommodate abutting ends of tubing within a range of tubing wall thicknesses.

SUMMARY OF THE INVENTION

The improved anastomotic device of the present invention is characterized by one or more engageable, locking slots as carried by mating prongs and a plurality of pawls carried by separate prongs which cooperatively join two ring members and retain the ring members in a preselected relationship with each other after being closed from the open position. Because the distance between the ring members can be varied in the manufacturing process to accommodate different thicknesses of tubular member walls, the device can be used in a variety of differing circumstances. The ring members and affixed prongs are so designed that they consist of a single unitary member that can be injection-molded. Two such molded parts can be put together without difficulty so that an anastomotic device capable of mass production and easy assembly is provided.

BRIEF DESCRIPTION OF THE DRAWINGS

Further details are explained below with the help of examples illustrated in the attached drawing wherein like characters of reference designate like parts throughout the several views and in which:

FIG. 2 is a bottom view of a single unitary member of a first embodiment of the anastomotic device having two such members comprising the present invention and shown in FIG. 1;

FIG. 3 is a side elevational and sectional view of a first embodiment of the anastomotic device according to the present invention including two unitary members like that shown in FIG. 2 and shown in solid lines in an engaged but unlocked position and in broken lines in an engaged and locked position;

FIG. 4 is a side and sectional elevational view of the single unitary member of FIG. 2 having a single ring member and an associated mating prong with locking notches and separate prong with pawls formed therein;

FIG. 5 is a top view of the single unitary member shown in FIG. 4;

FIG. 6 is a fragmentary, sectional view of the locking notches carried by the mating prong shown in FIG. 4;

FIG. 7 is an isolated side elevational and section view of the single unitary member shown in FIG. 4 showing an engaging pawl carried by the separate prong;

DETAILED DESCRIPTION OF THE INVENTION

Figure 1:
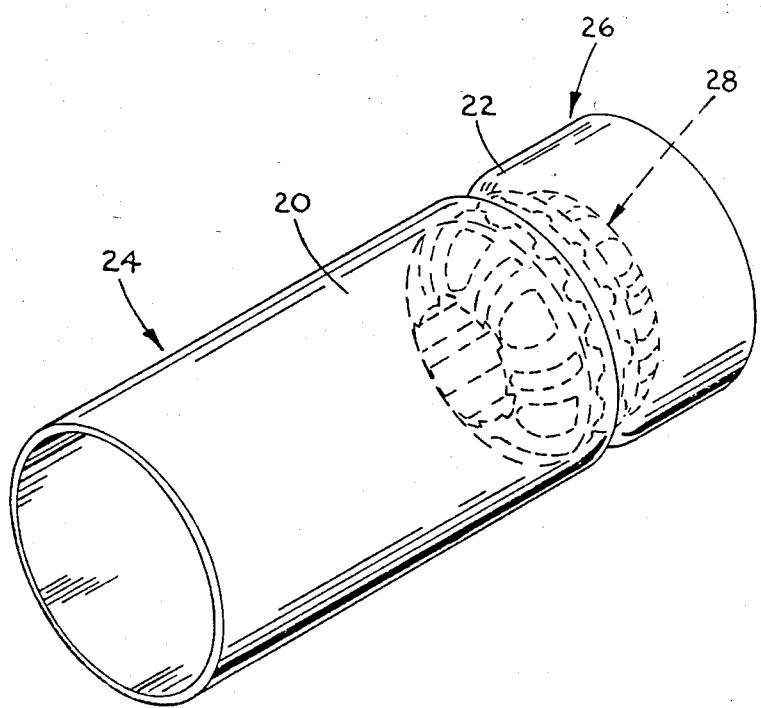
FIG. 1 is a perspective view of an anastomotic device made in accordance with the present invention shown in broken lines in the closed position and positioned to join the free ends of a tubular member in a contiguous relationship with each other.

Referring now to the drawings and particularly to FIG. 1, the free ends 20 and 22 of two tubular tissue members, shown here as cut ends of intestinal tracts and referred to generally as 24 and 26, have been anastomosed by using the device comprising the present invention shown by broken lines in outline form and designated generally as 28.

A first embodiment of anastomotic device 28 is shown in FIG. 3 while a single unitary member, two of which make up device 28, is shown generally as 30 in FIGS. 2, 4 and 5. Member 30 is made up of a ring member 32 having a plurality of slots 34 and apertures 36 about its periphery, a mating prong 38 which extends from ring member 32 in a direction substantially parallel to the center line of the ring member, and a separate prong 39 having engaging pawls formed therein. Mating prong 38 and separate prong 39 extending from the ring member 32 forms approximately one-half of an annular coupling tube 40 since they form approximately one-half of the inner and outer portions of ring member 32 as illustrated in FIG. 5.

Each mating prong 38 carries a plurality of locking slots 43, designed and positioned to mate cooperatively with engaging pawls 42 formed on the surface of separate prong 39. Each engaging pawl 42 is designed with a sloping forward edge 44 to facilitate easy relative motion when two unitary members 30 are joined and urgered operatively together. Pawls 42 each have a vertical engaging edge 46 which functions with slots 43 to lock members 30 in place and form anastomotic device 28.

Figure 13:
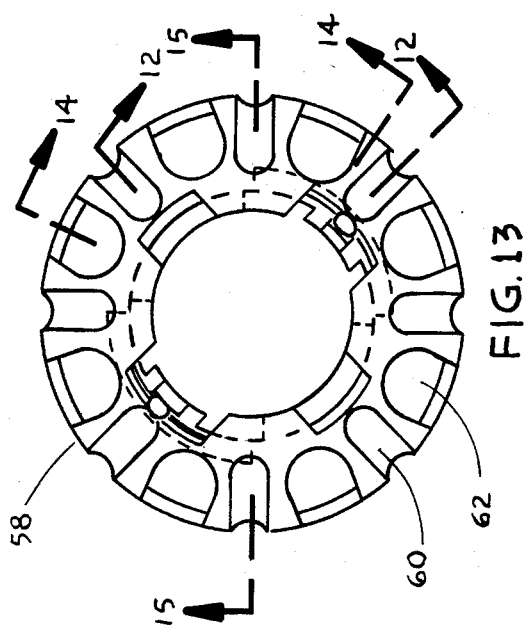
FIG. 13 is a top view of the single unitary member shown in FIG. 12.
Figure 15:
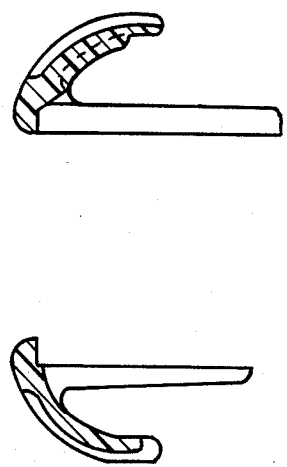
FIG. 15 is an isolated side elevational view of the single unitary member shown in FIG. 13 taken along line 15—15.
Figure 10:
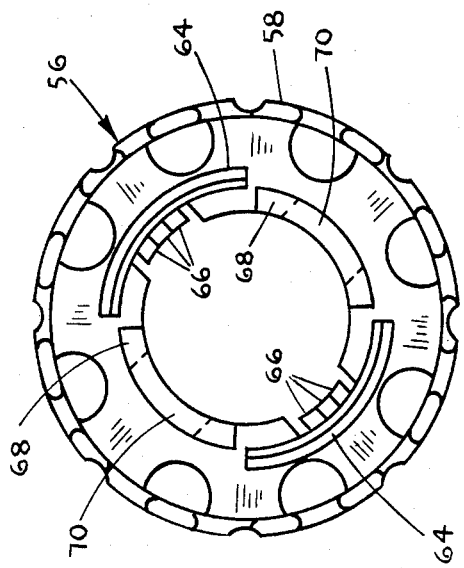
FIG. 10 is a plan view of a single unitary member of a second embodiment of the anastomotic device comprising the present invention.
Figure 11:
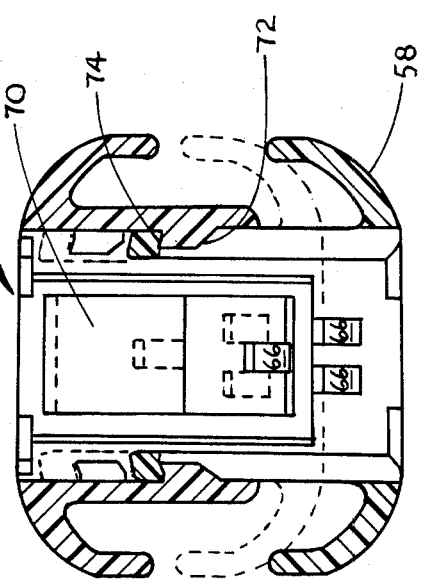
FIG. 11 is a side view of a second embodiment of the anastomotic device according to the present invention shown in solid lines in an engaged but unlocked position and in broken lines in an engaged and locked position.

A second embodiment of anastomotic device 28 is shown in complete form in FIG. 11 while a single unitary member, two of which make up this embodiment of device 28, is shown generally as 56 in FIGS. 10 and 13. Member 56 is made up of a ring member 58 having a plurality of slots 60 and apertures 62 about its periphery and a pair of oppositely positioned depending legs 64, each supporting a plurality of engaging pawls shown generally as 66. Alternately positioned between depending legs 64 and opposite each other are depending members 68, each of which has a pawl-engaging recess 70 to cooperatively receive pawls 66 when the two unitary members 56 are joined together to form anastomotic device 28.

Figure 12:
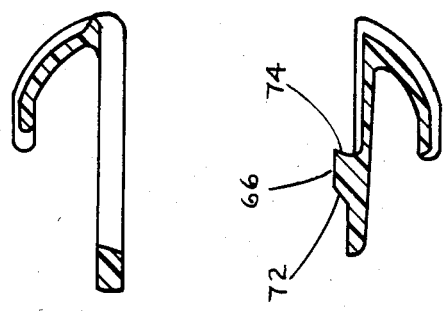
FIG. 12 is a side elevational view of the single unitary member of FIG. 2 having a single ring member and an associated mating prong with locking notches and a separate prong with engaging pawls formed therein.
Figure 14:
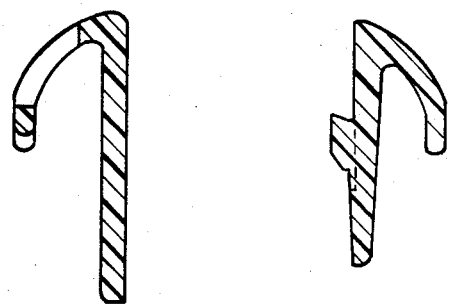
FIG. 14 is a fragmentary sectional view of the single unitary member shown in FIG. 13 taken along line 14—14.

Each pawl 66 carried by depending legs 64 has a partially sloped forward edge of 72 to facilitate easy motion when the two unitary members 56 are joined and urged together. Each pawl 66 has a somewhat inwardly curved engaging edge 74 as shown in FIG. 12 which functions with pawl-receiving recess 70 to lock unitary members 56 in place and form anastomotic device 28.

Figure 17:
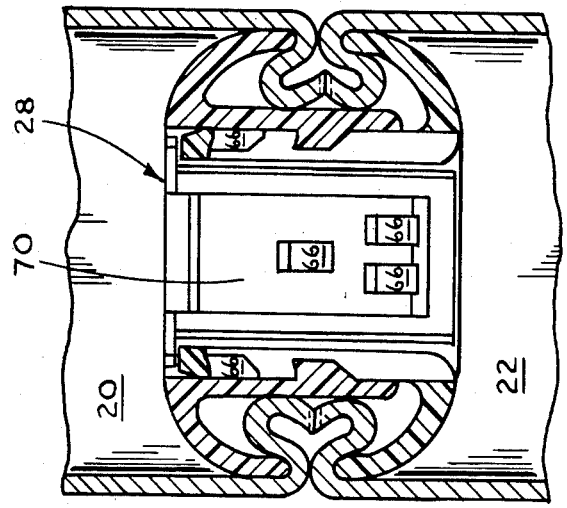
FIG. 17 is a sectional view of the second embodiment of the anastomotic device comprising the present invention joining the free ends of the tubular member with the device in the closed position.
Figure 16:
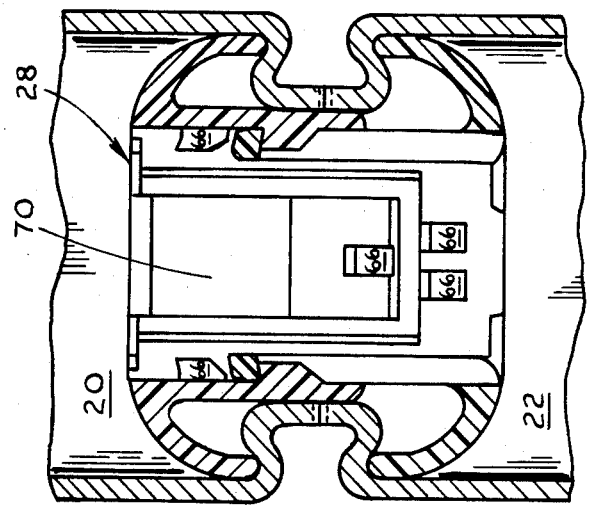
FIG. 16 is a sectional view of the second embodiment of the anastomotic device comprising the present invention joining the free ends of a tubular member with the device in the open or unlocked position.
Figure 18:
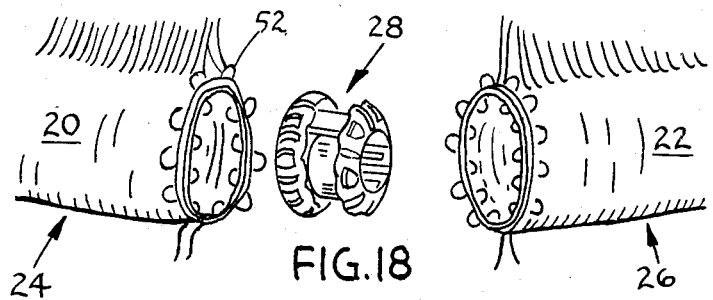
FIG. 18 is a perspective view of the anastomotic device forming the present invention functionally displaced from the free ends of a tubular member to be attached thereto.
Figure 19:
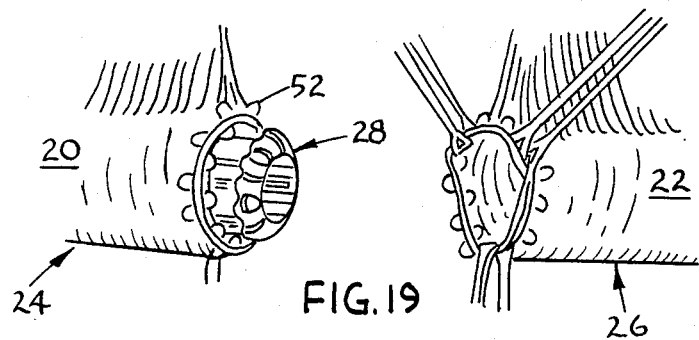
FIG. 19 is a perspective view wherein the anastomotic device has been attached to one end of the tubular member.
Figure 20:
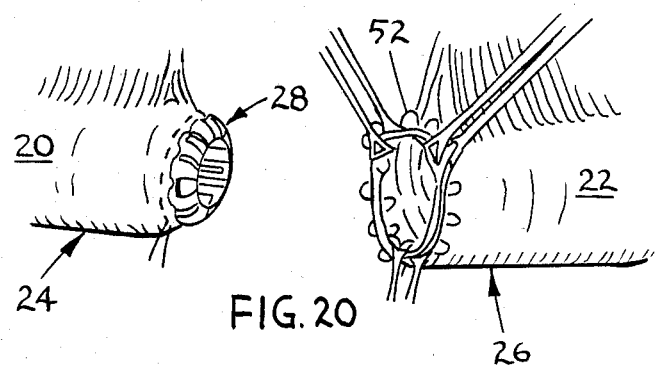
FIG. 20 is a perspective view similar to FIGS. 10 and 11 wherein one end of the tubular member has been tightened about the anastomotic device forming the present invention by a purse-string suture.
Figure 21:
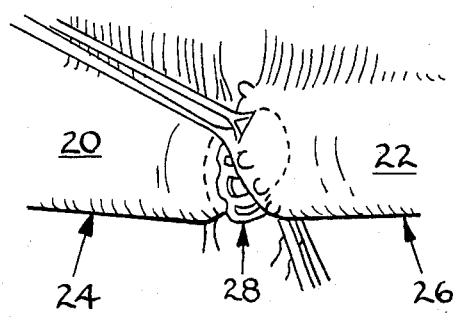
FIG. 21 is a perspective view of the anastomotic device forming the present invention wherein the second end of a severed tubular member is being pulled across the free ring member for subsequent connection thereto.
Figure 22:
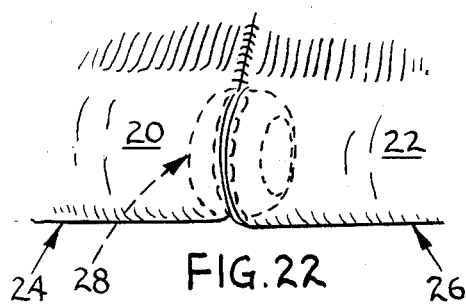
FIG. 22 is a perspective view of the anastomotic device forming the present invention which is functionally positioned to join the free ends of a tubular member for coupling in the closed position.

In the second embodiment of the anastomotic device pawls 66 are selectively positioned on each depending leg 64 of unitary member 56 to enable the anastomotic device 28 formed from two members 56 to be positioned in a first fixed position as shown in solid lines in FIG. 11 or in a second fixed position with the members closer together as shown in combined solid and broken lines in FIG. 11. The first and second fixed positions are also illustrated in FIGS. 16 and 17 respectively. Obviously any number of pawls can be positioned on depending legs 66 to achieve other desired positions.

It is necessary that members 30 and 56 forming two embodiments of device 28 be made from a material that will permit disintegration of the device in a relatively short period of time once healing of the vessel ends commences. Acceptable materials for forming the device are disclosed in U.S. Pat. No. 3,297,033 and are referred to as poly-hydroxyacetic ester and lactide copolymers. Molded surgical articles made from a wide range of glycolide/lactide copolymers have been known and utilized for quite some time.

Figure 8:
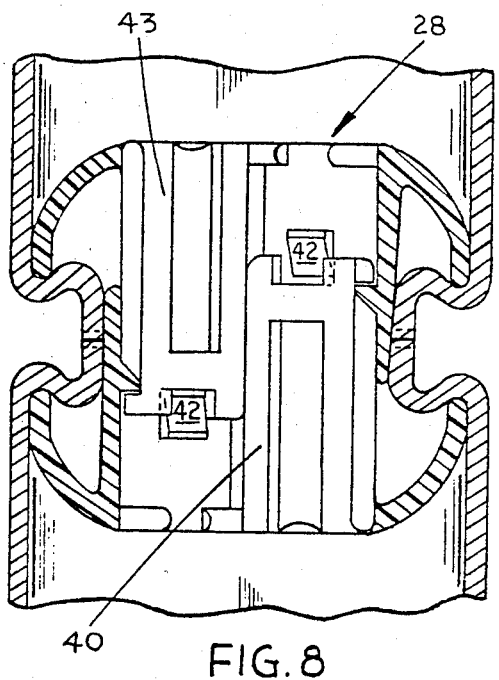
FIG. 8 is a sectional view of a first embodiment of the anastomotic device comprising the present invention joining the free ends of a tubular member with the device in the open or unlocked position.

Use of the first embodiment of the anastomotic device forming the present invention is shown in FIGS. 18 through 22 wherein the free ends 20 and 22 of tubular members 24 and 26 are stitched with a purse-string suture 52. Use of this suture permits engaging the very edge of the free end of the vessel wall so that the suturing material can be pulled and the vessel end contracted much in the way the top of a purse or string-closed bag is manipulated. The ends 20 and 22 are then pulled over each ring member 32 so that as the suture is tightened, the ends 20 and 22 of the vessel 24 and 26 are turned inwardly over ring members 32 as shown in FIG. 8. The members 32 are then urged together until the pawls 42 on the separate prongs 39 are engaged within the slots 43 on the mating prongs 38, thus forming the connected annular coupling tube 40 of the device 28. When members 32 are in the appropriate relationship by the formation of annular coupling tube 40, the free ends of the two tubular members are contiguously positioned in a manner that will enable them to grow together permanently as shown in FIG. 9.

The device 28 provides ample space for the anastomosis to be performed after the members 32 are urged together and the mating prongs 38 engage with each other to form the annular coupling tube 40. Coupling tube 40 is sturdy as a result of its formation by two contiguous rings of alternating mating and separate prongs best shown in FIGS. 5 and 13. Both members 30 and 56 have approximately one-half of an outer ring formed by the separate prong 39 in FIG. 1 and approximately one-half of an inner ring formed by the mating prong 38. Bowel tissue is mechanically held together by the force of the purse-string suture against the annular coupling tube 40 and the clamping force of the ring members compressing the two ends together.

Note that the edges 80 and 82 of member ends 20 and 22 are positioned to abut in an edge-to-edge relationship when the suture is tightened since the diameter of annular coupling tube 40 is not much smaller than the diameter of the ring 32, thus resulting in a relatively unobstructed passageway through which fluids and gases may flow.

Figure 9:
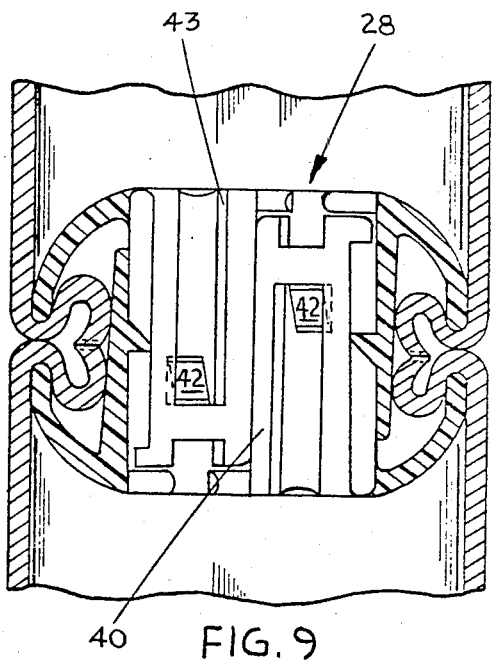
FIG. 9 is a sectional view of a first embodiment of the anastomotic device comprising the present invention joining the free ends of a tubular member with the device in the closed position.

After member ends 20 and 22 are secured by sutures 52, ring members 32 are then urged together until the pawls 42 on the separate prongs 39 are engaged within the slots 43 on the mating prongs 38, thus forming the completed and connected annular coupling tube 40 as shown in FIG. 9. When ring members 52 are in the appropriate relationship and the formation of annular coupling tube 40 is complete, the ends of the members 20 and 22 are contiguously positioned at their edges 80 and 82 and at second adjacent locations 84 and 86 as shown in FIG. 9. Positioning the two tubular members in this manner will enable them to grow together permanently in the shortest amount of time.

A variety of diameters and spacings for the ring members and diameters for the annular coupling tube are desirable to provide needed versatility of use within the needed sizes for animals and humans. Moreover, there are certain unusual tubular configurations within humans and animals that might better respond to the use of a similarly constructed anastomotic device having elliptically shaped ring members and annular coupling tubes rather than the circular configuration shown in the embodiments shown herein. Such embodiments are viewed as being within the scope of this disclosure and the accompanying claims.

It is to be understood that the anastomotic device made of either the composite materials referenced above or of a newly developed material which is disclosed in U.S. patent application Ser. No. 198,565 filed Oct. 20, 1980, abandoned and assigned to American Cyanamid Company and incorporated herein by reference can be designed to disintegrate, preferably through fragmentation, in a given period of time. Such material offers many advantages over conventional anastomotic devices and permits simple, rapid anastomosis in difficult areas. For example, it permits a simpler anastomosis in a low rectosigmoid anastomosis which ordinarily would be quite time-consuming and difficult, perhaps requiring temporary colostomy, or ever being impossible in those cases necessitating a permanent colostomy.

It will be apparent that the present invention is comprised basically of two single unitary members, each having a disintegratable ring member and either a connected mating prong or depending legs and recess-forming members which cooperatively unite to form the embodiments described herein. However, the invention in its broader aspects is not limited to the specific embodiments herein shown and described, and departures may be made therefrom within the scope of the accompanying claims without departing from its principles and without sacrificing its chief advantages.

What is claimed is:

1. An anastomosis device for use in the surgical joining of the free ends of two tubular members to be anastomosed, said device comprising: a pair of identical ring members for securement to the free end of each of the tubular members to be anastomosed; at least one mating prong and one separate prong integral with and depending from each of said ring members, and prongs cooperatively mating with each other to form an annular coupling tube connecting said ring members; cooperatively connectable engaging pawls and locking slots formed in said separate and mating prongs enabling the securement of said ring members at first and second predetermined distances from each other whereby said tubular member free ends are ultimately positioned contiguous to each other proximate said ring members and said engaged separate and mating prongs; suture means extending around each tubular member free end pulling and holding said free end proximate said ring member and said engaged and separate mating prongs forming said annular coupling tube, and contiguous to the other tubular member free end whereby said engaging pawls engage said locking slots and secure said ring members at a first predetermined distance from each other to enable the positioning of said tubular member free ends proximate said ring members and the placement of said purse-string suture there around and said engaging pawls engage said locking slots and secure said ring members at a second predetermined distance from each other when said ring members are moved toward each other to position said tubular member free ends contiguous to each other without penetrating the tubular member free ends and enable said free ends to grow together and approximate the inner, middle and outer surfaces of the tubular member without necrosis.

2. The device as claimed in claim 1 wherein the number of integral mating prongs on each ring member is at least one pair and the number of separate prongs on each ring member is at least one pair.

3. The device as claimed in claim 2 wherein said coupling tube has a constant inner diameter.

4. The device as claimed in claim 3 wherein said ring members, said prongs, and said press-string suture are formed of a disintegratable material.

5. The device as in claim 2 wherein said ring members, said prong, and said purse-string suture are formed of a disintegratable material.

6. The amendment as claimed in claim 2 wherein said connecting means includes a purse-string suture extending around said tubular member free ends pulling said free ends over said ring members and in close engagement with said annular coupling tube, said tubular member free ends having terminal edges, being contiguous at said terminal edges, and being contiguous at a second location near said terminal edges.

7. The device as claimed in claim 1 wherein said coupling tube has a constant inner diameter.

8. The device as claimed in claim 7 wherein said ring members, said prongs, and said purse-string suture are formed of a disintegratable material.

9. The device as claimed in claim 1 wherein said tubular member free ends are ultimately positioned over said ring members and around said annular connecting means, said tubular member free ends having terminal edges, being contiguous at said terminal edges and being contiguous at a second location near said terminal edges.

10. The device as claimed in claim 9 wherein said ring members, said prongs, and said purse-string suture are formed of a disintegratable material.

11. The improvement as claimed in claim 1 wherein said securement enabling means includes a plurality of engaging pawls formed on said separate prongs and positioned to mate cooperatively with said locking slots on said mating prongs to secure said prongs and ring members in a preselected relationship and thereby retain said ring members at a preselected distance from each other to accommodate penetration the free ends of the two tubular members.

* * * * *